United States Patent [19]

Hsu

[11] Patent Number: 5,112,382
[45] Date of Patent: May 12, 1992

[54] HALOPROPARGYL COMPOUNDS, COMPOSITIONS, USES AND PROCESSES OF PREPARATION

[75] Inventor: Adam C. Hsu, Lansdale, Pa.

[73] Assignee: Rohm and Haas Company, Philadelphia, Pa.

[21] Appl. No.: 528,653

[22] Filed: May 24, 1990

[51] Int. Cl.⁵ ............................................ C07D 257/04
[52] U.S. Cl. .................................... 71/88; 549/473;
549/481; 549/482; 549/484; 549/488; 549/491;
549/493; 549/496; 549/60; 549/68; 549/77;
549/472; 71/90; 71/92; 71/93; 71/98; 71/105;
71/106; 71/111; 71/113; 71/DIG. 1; 558/411;
558/414; 558/415; 564/148; 564/149; 564/151;
514/397; 514/399; 514/444; 514/448; 514/471;
514/519; 514/521; 514/523; 514/614; 514/615;
548/255; 548/262.2; 548/264.8; 548/266.6;
548/267.4; 548/336; 548/337; 548/339;
548/341
[58] Field of Search .............. 549/482, 484, 491, 496,
549/68, 76, 74, 77; 560/22, 23, 30, 31, 34;
71/88, 90, 92, 93, 98, 106, 113, 114, 111, DIG.1,
105

[56] References Cited

U.S. PATENT DOCUMENTS

| | | | |
|---|---|---|---|
| 2,319,481 | 5/1943 | Stillman et al. | 549/482 |
| 4,065,565 | 12/1977 | Sasajima et al. | 504/148 |
| 4,201,785 | 5/1980 | Kathawale | 564/148 |
| 4,298,626 | 1/1981 | Punja et al. | 549/482 |
| 4,344,893 | 8/1982 | Copping et al. | 564/148 |
| 4,520,023 | 5/1985 | Schmitt et al. | 514/241 |
| 4,616,004 | 10/1986 | Edwards | 514/63 |
| 4,639,460 | 1/1987 | Rose | 514/369 |

Primary Examiner—C. Warren Ivy
Assistant Examiner—Raymond Covington
Attorney, Agent, or Firm—Michael B. Fein

[57] ABSTRACT

Compounds of the formula

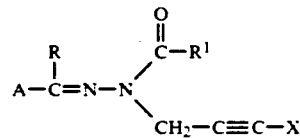

wherein

A is selected from the group consisting of (1) phenyl, (2) naphthyl, (3) phenyl substituted with one or more halo, cyano, ($C_1$-$C_4$) alkyl, nitro, ($C_1$-$C_4$)haloalkyl, and ($C_1$-$C_4$)thioalkyl, (4) naphthyl substituted with one or more halo, cyano, ($C_1$-$C_4$)alkyl, nitro, ($C_1$-$C_4$), and ($C_1$-$C_4$) thioalkyl, (5) thiophene, (6) furan, (7) thiophene substituted with one or more substituents selected from halo and nitro, and (8) furan substituted with one or more substituents selected from halo and nitro;

R disclose as microbicidally and fungicidally active.

8 Claims, No Drawings

HALOPROPARGYL COMPOUNDS, COMPOSITIONS, USES AND PROCESSES OF PREPARATION

BACKGROUND OF THE INVENTION

1. Field of the Invention

This invention relates to control of microorganisms.

2. Description of the Prior Art

Certain classes of iodopropargyl compounds have been proposed as fungicides or microbicides but no compound within those classes has achieved commercial success.

U.S. Pat. No. 4,616,004 to Edwards discloses fungicidal activity for compounds of the formula

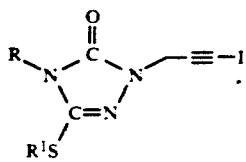

U.S. Pat. No. 4,639,460 to Rose shows compounds of the formula

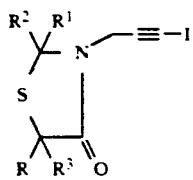

as fungicides

U.S. Pat. No. 4,520,023 to Schmitt shows 3-(3-iodopropargyl)benzo-1,2,3-triazolin-4-ones and their use as microbicidal agents.

There was no suggestion in the prior art that compounds within the formula of the present invention would have utility in controlling microorganisms.

SUMMARY OF THE INVENTION

It is an object of the present invention to provide new compounds for controlling microorganisms.

A further object is to provide methods of making such compounds, methods of using them, compositions comprising such compounds, and uses of such compositions.

These objects, and others which will become apparent from the following disclosure, are achieved by the present invention which comprises in one aspect compounds of the formula

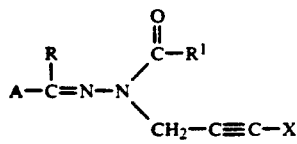

wherein

A is selected from the group consisting of (1) phenyl, (2) naphthyl, (3) phenyl substituted with one or more halo, cyano, $(C_1-C_4)$alkyl, nitro, $(C_1-C_4)$haloalkyl, and $(C_1-C_4)$thioalkyl, (4) naphthyl substituted with one or more halo, cyano, $(C_1-C_4)$alkyl, nitro, $(C_1-C_4)$haloalkyl, and $(C_1-C_4)$thioalkyl, (5) thiophene, (6) furan, (7) thiophene substituted with one or more substituents selected from halo and nitro, and (8) furan substituted with one or more substituents selected from halo and nitro;

R is selected from the group consisting of hydrogen, $(C_1-C_4)$alkyl and substituted or unsubstituted phenyl wherein the substituents are selected from one or more halo, cyano, $(C_1-C_4)$alkyl, nitro, $(C_1-C_4)$haloalkyl, and $(C_1-C_4)$thioalkyl;

$R^1$ is selected from the group consisting of $(C_1-C_4)$alkoxy; hydrogen; optionally substituted phenyl wherein the phenyl substituents are selected from the group consisting of halo, cyano, $(C_1-C_4)$alkyl, nitro, $(C_1-C_4)$haloalkyl, and $(C_1-C_4)$thioalkyl; $(C_1-C_8)$alkyl; and optionally substituted heterocycles wherein said heterocycles are selected from the group consisting of thiophene, furan, imidazole, and triazole, which are optionally substituted with $(C_1-C_3)$alkyl, halo, and nitro; and X is selected from the group consisting of I and Br.

In another aspect the invention comprises a method of preparing such compound comprising reacting a compound of the formula

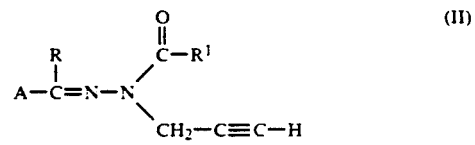

with an iodating or brominating agent.

A further aspect comprises a composition comprising the compounds, or the compound itself, to protect a material selected from the group consisting of wood, paint, adhesive, glue, paper, textile, leather, plastics, cardboard, lubricants, cosmetics, food, caulking, feed and industrial cooling water from microorganisms.

DETAILED DESCRIPTION OF THE INVENTION AND THE PREFERRED EMBODIMENT

The compounds of the invention are of formula I as set forth above. The more preferred embodiments are the following compounds:

1. N'-Methoxycarbonyl-N'-3-bromopropargyl 4-chlorobenzaldehyde hydrazone
2. N'-Formyl-N'-3-bromopropargyl 4-chlorobenzaldehyde hydrazone
3. N'-Methoxycarbonyl-N'-3-iodopropargyl benzaldehyde hyrazone
4. N'-Methoxycarbonyl-N'-3-iodopropargyl 4-methylbenzaldehyde hydrazone
5. N'-Methoxycarbonyl-N'-3-iodopropargyl 4-chlorobenzaldehyde hydrazone
6. N'-Benzoyl-N'-3-iodopropargyl benzaldehyde hydrazone
7. N'-Methoxycarbonyl-N'-3-bromopropargyl 4-fluorobenzaldehyde hydrazone
8. N'-Methoxycarbonyl-N'-3-iodopropargyl 5-nitro-2-furancarboxaldehyde hydrazone
9. N'-Methoxycarbonyl-N'-3-iodopropargyl 4-cyanobenzaldehyde hydrazone
10. N'-Methoxycarbonyl-N'-3-iodopropargyl 4-fluorobenzaldehyde hydrazone
11. N'-Methoxycarbonyl-N'-3-iodopropargyl 3,4-dichlorobenzaldehyde hydrazone 12. N'-Benzoyl-N'-3-iodopropargyl 3-nitrobenzaldehyde hydrazone
13. N'-Ethoxycarbonyl-N'-3-iodopropargyl 3,4-dichlorobenzaldehyde hydrazone
14. N'-Ethoxycarbonyl-N'-3-bromopropargyl 3,4-dichlorobenzaldehyde hydrazone
15. N'-Methoxycarbonyl-N'-3-iodopropargyl 3,5-dichlorobenzaldehyde hydrazone
16. N'-Methoxycarbonyl-N'-3-bromopropargyl 3,5-dichlorobenzaldehyde hydrazone The iodopropargyl compounds, i.e., those wherein X is I, are preferred.

As stated above, compositions comprising a compound according to formula I and either an agronomically acceptable carrier, a cosmetic agent, a cutting oil, a soap or synthetic detergent, a stabilizer, a film-forming material, or the like have a wide range of utility for protecting against or controlling microorganisms from a wide variety of classes including fungus, bacteria, algae, viruses and yeasts. The preferred utilities of the compositions are to protect wood, paint, adhesive, glue, paper, textile, leather, plastics, cardboard, lubricants, cosmetics, food caulking, feed and industrial cooling water from microorganisms.

The following list specific industries and applications of the compounds or compositions:

| Industry | Application |
| --- | --- |
| Adhesives, sealants | adhesives |
|  | caulks |
|  | sealants |
| Agriculture/food chain | adjuvant preservation |
|  | agricultural active ingredient |
|  | agricultural chemical preservative |
|  | agricultural formulations preservation |
|  | animal feed preservation |
|  | dairy chemicals |
|  | fertilizer preservation |
|  | food preservation |
|  | food processing chemicals |
|  | grain preservation |
|  | post-harvest produce protection |
|  | sugar processing |
|  | tobacco |
| Construction products | asphalt/concrete |
|  | cement modifiers |
|  | construction products |
|  | roof mastics |
|  | synthetic stucco |
|  | wall mastics |
|  | joint cement |
| Cosmetics and toiletries | cosmetics |
|  | raw materials for cosmetics, toiletries |
|  | toiletries |
| Disinfectants, antiseptics | antiseptic |
|  | disinfectant |
| Emulsions, dispersions | aqueous dispersions |
|  | dispersed pigments |
|  | latex |
|  | photographic emulsions |
|  | pigment slurries |
|  | polymer latices |
| Formulated consumer & industrial products | air fresheners |
|  | fabric softeners |
|  | hand cleaners |
|  | polishes, floor, furniture, shoe |
|  | sponges & towelettes |
|  | spray starch |
|  | waxes |

| Industry | Application |
| --- | --- |
| Industrial processing, misc | dry cleaning fluids preservation |
|  | electrodeposition paint, baths, rinses. |
|  | electrodeposition pre-treatment. |
|  | post rinses |
|  | industrial fluids preservation |
|  | pasteurization baths |
|  | process aid preservation |
| Industrial water treatment | air washers |
|  | cooling towers |
|  | cooling water |
|  | water cooling |
| Laundry | household laundry products |
|  | laundered goods |
|  | laundry wash water |
|  | pre-washers |
|  | sanitizers-laundry |
|  | removers, spot & stain |
| Leather, leather products | leather and hide |
|  | leather and hide products |
| Lubricants, hydraulic aids | automotive lubricants and fluids |
|  | conveyor lubricants |
|  | greases |
|  | hydraulic fluids |
|  | hydraulic oils |
|  | lubricants |
| Medical devices | diagnostic enzymes |
|  | diagnostic kits |
|  | medical devices |
| Metalworking & related app's | cutting fluids |
|  | metal cleaning |
|  | metalworking fluids |
| Odor control (active ingredient) | air conditioning |
|  | animal bedding |
|  | cat litter |
|  | chemical toilet prep'ns |
|  | deodorizers |
|  | humidifiers |
|  | industrial deodorants |
|  | sanitary formulations |
|  | toilet bowls |
| Paints and coatings | coating emulsions |
|  | paints |
| Paper and wood pulp, their products | absorbant materials of paper and wood pulp |
|  | packaging materials of paper and wood pulp |
|  | paper |
|  | paper products |
|  | paper treatment |
|  | soap wrap |
|  | wood pulp |
|  | wood pulp products |
| Paper mill | paper mill slimicides |
|  | pulp and paper slurries |
| Petroleum refining, fuels | aviation fuels (jet fuel, aviation gas) |
|  | burner, diesel and turbine fuel oils |
|  | coal slurries |
|  | diesel fuel additives |
|  | diesel fuels |
|  | fuels |
|  | gasoline |
|  | heating oils |
|  | hydrocarbons |
|  | kerosene |
|  | liquefied petroleum gas |
|  | petrochemical feedstocks |
|  | petroleum products, storage, transportation and production |
|  | recycled petroleum products |
|  | residual fuel oils |
|  | turbine oils |

| Industry | Application |
| --- | --- |
| Photographic chemicals and process | photographic processing - wash water, rinses photoplate processing chemicals (developers, stabilizers etc) |
| Printing | fountain solutions (printing) ink components (pigments, resins, solvents, etc) inks |
| Sanitizers (active) | sanitizers sanitizers-dairy sanitizers-dental sanitizers-fermentation sanitizers-food preparation sanitizers-food processing sanitizers-medical sanitizers-rendering sanitizers-veterinary |
| Soaps, detergents, cleaners | cleaners· detergents, hand automatic laundry, other industrial cleaners liquid soaps, hand, dish, laundry oil and grease remover powdered soaps raw materials for cleaning products soaps surfactants |
| Textiles, textile products | bonded fabrics burlap canvas canvas goods carpet backing carpets clothing coated fabrics curtains draperies engineering textiles fibers geotextiles goods made of textiles knitted fabrics nets nonwoven fabrics rope rugs textile accessories textile products textiles upholstery woven fabrics yarn |
| Textile processing | dye fixatives dyes fiber lubricants hand modifiers sizes textile processing fluids |
| Therapeutic (active or preservative) | animal health/veterinary aquaculture dental human health pharmaceutical/therapeutic |
| Water purification | charcoal beds deionization resins filters membranes reverse osmosis membranes ultrafilters water purification water purification pipes, tubing |
| Wood applications | lazures (wood stains) wood |

| Industry | Application |
| --- | --- |
| Miscellaneous | wood products alcohols bedding incorporating water or gels ceramic contact lens cases-leaching electronic circuitry electronics chemicals enzymes-food production enzymes-industrial gel cushions laboratory reagents marine antifoulants mildewcides mining applications natural rubber latex oil field applications pipes plastics polymer systems polymers and resins (synthetic and natural) reagent preservation rubber rubber products skin remover solid protective/decorative films swimming pools waste treatment water beds |

The amounts of the compound to be used depend on the application. The useful amounts for a particular application are similar to amounts used for other microbicide compounds.

The compound can be used in combination with other microbicides. The term "microbicide" is considered equivalent to "antimicrobial" as used herein.

Compounds of formula I can be prepared by a variety of methods. One suitable method comprises reacting a compound of formula II with an iodinating or brominating agent.

Suitable iodinating or brominating agents include, for example, iodine, bromine, an iodine-amino compound such as morpholine-iodine complex, morpholine-bromine complex, N-bromosuccinimide ("NBS") and N-iodosuccinimide ("NIS"), the latter being the most preferred.

When an iodine, bromine, or iodo-amino compound is used, base should also be used, preferably sodium or potassium hydroxide, and solvent such as methanol, ethanol, and aqueous ethanol should also be used.

When NIS or NBS is used, a catalyst such as, for example, silver nitrate, or the like, should be used in presence of solvent such as acetone, methyl ethyl ketone, tetrahydrofuran, and the like.

Reaction times of about 20 minutes to about 24 hours have been utilized successfully with reaction temperatures of about 0° C. to about 25° C.

Suitable methods of application of compounds of formula I to control fungi, bacteria, algae, viruses, yeasts, and the like are in amounts and with carriers, etc., as well known in the art.

The following examples are presented to illustrate a few embodiments of the invention. All parts and percentages are by weight unless otherwise indicated.

Table (1) shows the structures and the physical data of the preferred respective compounds.

TABLE 1

Physical Data

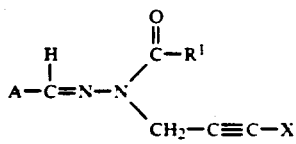

| No. | A | R' | X | Melting Point |
|---|---|---|---|---|
| 1 | 4-Cl—Ph | OMe | Br | 102–105° C. |
| 2 | 4-Cl—Ph | H | Br | 135–140° C. |
| 3 | Ph | OMe | I | 149–151° C. |
| 4 | 4-Me—Ph | OME | I | 112–116° C. |
| 5 | 4-Cl—Ph | OMe | I | 143–146° C. |
| 6 | Ph | Ph | I | 109–111° C. |
| 7 | 4-F—Ph | OMe | Br | 86–91° C. |
| 8 | 5-NO$_2$-furan | OMe | I | — |
| 9 | 4-CN—Ph | OMe | I | 126–132° C. |
| 10 | 4-F—Ph | OMe | I | — |
| 11 | 3,4-Cl$_2$—Ph | OMe | I | 110–118° C. |
| 12 | 3-NO$_2$—Ph | Ph | I | 139–145° C. |
| 13 | 3,4-Cl$_2$—Ph | OEt | I | 169–170° C. |
| 14 | 3,4-Cl$_2$—Ph | OEt | Br | 148–149° C. |
| 15 | 3,5-Cl$_2$—Ph | OMe | I | 183–184° C. |
| 16 | 3,5-Cl$_2$—Ph | OMe | Br | 141–142° C. |

EXAMPLE 1

Preparation of
N'-methoxycarbonyl-N'-3-bromopropargyl
4-chlorobenzaldehyde hydrazone To the suspension of N'-methoxycarbonyl 4-chlorobenzaldehyde hydrazone (4.0 g, 0.0188 mole) in dry acetone (50 ml) at room temperature under nitrogen was added potassium carbonate (3.9 g, 0.028 mole), followed by propargyl bromide (3.4 g, 0.028 mole) with magnetic stirring. The reaction mixture was refluxed for 24 hr. The reaction mixture was cooled down to room temperature and was poured into water (200 ml). The resultant precipitate was collected by suction-filtration affording 4.7 g (99% yield) of N'-methoxycarbonyl-N'-propargyl 4-chlorobenzaldehyde hydrazone, m.p.=102°–105° C. An NMR spectrum showed the desired compound.

This intermediate was used for the next step without further purification.

To the suspension of N'-methoxycarbonyl-N'-propargyl 4-chloro-benzaldehyde hydrazone (1.25 g, 0.005 mole) in dry acetone (40 ml) at room temperature with magnetic stirring was added N-bromo-succinimide (1.03 g, 0.0058 mole), followed by silver nitrate (0.011 g, 0.00065 mole). The reaction mixture was stirred at room temperature for 1 hr. The purple reaction mixture was poured into water and the resultant precipitate was collected by suction-filtration to give a crude product. The crude product was dissolved in ethyl acetate (50 ml), dried over anhydrous sodium sulfate, and filtered to get a colorless solution. The solvent was evaporated on a rotary evaporator affording 1.10 g (67.1% yield) of N'methoxycarbonyl-N'-3-bromopropargyl 4-chlorobenzaldehyde hydrazone as a solid. m.p.=102°–105° C. An NMR spectrum showed the desired compound.

EXAMPLE 2

Biocidal Evaluations of Compounds

A minimum inhibitory concentration (MIC) value is obtained using a broth, two-fold serial dilution test performed as follows: A stock solution of dispersion of the test compound, typically at a concentration of 1%, is made in a 5:3:2 solvent solution of acetone, methanol, and water. A volume of the stock solution is dispensed into culture media to give an initial starting test concentration of 500 ppm compound.

The test is carried out by adding and equal volume of broth to each vessel in the dilution series, except for the first vessel. The first vessel contains twice the volume of broth plus the initial concentration of test compound. One half of the broth from the first vessel is transferred to the second vessel. After being mixed, one half the resulting volume is removed from the second vessel and transferred to the third vessel. The entire cycle is repeated sufficiently to give a series of concentrations amounting to 500, 250, 125, 63, 31, 16, 8, and 4 ppm (or 100, 50, 25, 12.5, 6.2, 3.1, 1.6, and 0.8), respectively.

Each vessel is then inoculated with a cell suspension of the appropriate test organism. Bacteria are grown in both and fungi on agar slats for a time and at a temperature appropriate to the species being tested. At the end of the growth period, the broth is vortexed to disperse the cells. In the case of fungi, the pores are harvested by pipetting water onto the slant and dislodging the spores with a sterile loop. The cell/spore suspension is standardized by controlling incubation time, temperature, and the volume of the diluent. The suspension is then used to inoculate the vessels containing the broth compound. The vessels are then incubated at the appropriate temperature. After the incubation, the vessels are examined for growth/no growth. The minimum inhibitory concentration (MIC) is defined as the lowest concentration of compound that results in complete inhibition of growth of the test organism.

The organisms tested to demonstrate biocidal activity include:

BACTERIA

*Pseudomonas fluorescens* (Psfl)
*Pseudomonas aerugenosa* (Psae)
*Escherichia coli* (Ecol)
*Staphylococcus aureus* (Saur)

FUNGI

*Aspergillus niger* (Anig)
*Aureobasidium pullulans* (Apul)

TABLE 2

Biocidal Evaluation
The Result of Minimum Inhibitory Concentration (MIC) Tests

| Compound # | MIC (ppm) | | | | | |
|---|---|---|---|---|---|---|
| | Psfl | Psae | Ecol | Saur | Anig | Apul |
| 1 | >500 | 250 | >500 | >500 | >500 | 63 |
| 2 | >500 | 250 | >500 | >500 | >500 | 63 |
| 3 | >500 | 250 | >500 | 125 | <4 | <4 |
| 4 | 125 | 125 | 250 | 16 | <4 | 8 |
| 5 | 125 | 16 | 125 | 8 | <4 | <4 |
| 6 | 50 | 25 | 50 | 50 | 6 | 3 |
| 7 | 125 | 31 | 125 | 63 | 31 | 31 |
| 8 | 250 | 125 | 63 | <4 | <4 | <4 |
| 9 | >500 | >500 | >500 | >500 | >250 | — |
| 10 | >500 | >500 | >500 | <4 | <4 | <4 |
| 11 | >500 | >500 | >500 | 8 | <4 | <4 |
| 12 | >100 | >100 | >100 | >100 | >100 | 100 |
| 13 | >100 | >100 | >100 | >100 | 100 | >100 |
| 14 | >100 | >100 | >100 | >100 | >100 | >100 |
| 15 | >100 | >100 | >100 | >100 | >100 | >100 |
| 16 | >100 | >100 | >100 | >100 | >100 | >100 |

EXAMPLE 3

In-Vitro Plant Fungicide Tests of Compounds

The organisms employed in the test are:

| | |
|---|---|
| PYU | Pythium ultimum (Oomycete) |
| PHY | Phytophthora capsici (Oomycete) |
| PIR | Piricularia oryzae (Ascomycete) |
| HEL | Cochliobolus sativus (Ascomycete) |
| BOC | Botrytis cinerea (Ascomycete) |
| FUS | Fusarium roseum (Ascomycete) |
| SEP | Septoria nodorum (Ascomycete) |
| RHI | Rhizoctonia solani (Basidiomycete) |
| XAN | Xanthomonas campestris (basterium) |

METHODS

1. Culture maintenance: Transfers in steps 1 and 2 are done in a laminar flow hood. All 8 fungi and the bacterium used in this test are transferred and maintained on potato dextrose agar plates each week (2 plates/organism). Organisms are used when they are the following ages: a. 1 week old: PYU, PHY, RHI; b. 2 weeks old: XAN, PIR, BOC, HEL, FUS, SEP. *Pythium ultimum* and *Phytophthora capsici* are transferred to asparagine-sucrose broth shake cultures (ASB). *Rhizoctonia solani*, *Fusarium roseum*, and *Zanthomonas campestris* are maintained in yeast extract-dextrose broth (YDB) on a shaker. Culture flasks are inoculated with 6 mycelial plugs each (except for Pythium which is inoculated with only 3 plugs) taken from PDA plates. All liquid shaker cultures are used after 2 days growth.

2. Inoculum preparation. Conidia and mycelium from PIR, BOC, HEL, and SEP, are lightly scraped off into YDB so that mostly conidia are used as inoculum. The conidial suspension is strained through a double layer of cheesecloth to remove mycelial clumps. One plate products enough conidia or mycelium to inoculate 100 ml of YDB. XAN broth cultures is poured (1 ml culture/100 ml broth) into YDB. PYU, PHY, RHI and FUS cultures are ground up (2–3 5 second burst in a blender) and all but Pythium and Phytophthora are filtered through a double layer of sterile cheesecloth to remove large mycelial clumps. Ten ml of the culture solutions of *R. solani* and *F. roseum* are added to 90 ml of YSP and 10 ml of the *P. capsici* is added to 90 ml ASB. Two ml of the culture solution of *P. ultimum* is added to 98 ml of ASB. Care must be made not to overinoculate (e.g. solutions should appear fairly clear to the eye, yet when held up to light a faint cloudiness should be visible) or standards will not behave properly. The inoculum mixtures are place in microtiter plates using a 12-tipped pipet. 175 μl (single dose) or 100 μl (dose-response test) of inoculum broth is placed in each well of the microtiter plates. The plates with inoculated media are placed in the refrigerator overnight. There are two replications per treatment.

3. Addition of compounds. This operation is carried out in a chemistry hood. Sic microtiter plates have 245 microliters of sterile water added to their wells ahead of time. 10 Mg a.i. of the compounds are placed in 1 ml 1:1 acetone:methanol. 5 Microliters of this solution is pipetted into the microtiter plates containing the sterile water according to the grid. There are 45 compounds and 3 scattered control treatments per plate. There are 2 replicates per treatment. 25 Microliters of solution is transferred to the inoculated plates with a 96 well replicator. The replicator is flame sterilized with alcohol, rinsed with sterile water, and blotted on sterile paper towels between each transfer.

TABLE 3

The Results of In-Vitro Plant Fungicide Tests

| Compound | Rate (PPM) | % Control | | | | | | | | |
|---|---|---|---|---|---|---|---|---|---|---|
| | | BOC | FUS | HEL | PHY | PIR | PYU | RHI | SEP | XAN |
| 1 | 25 | 0 | 0 | 0 | 0 | 0 | 0 | 0 | — | 0 |
| 2 | 25 | 0 | 0 | 0 | 75 | 50 | 0 | 0 | — | 0 |
| 3 | 25 | 0 | 75 | 0 | 75 | 0 | 75 | 100 | — | 0 |
| | 50 | 0 | 100 | 0 | 100 | 95 | 100 | 100 | 75 | 0 |
| 4 | — | — | — | — | — | — | — | — | — | — |
| 5 | 25 | 0 | 95 | 100 | 50 | 100 | 50 | 75 | — | 0 |
| 6 | 25 | 0 | 0 | 0 | 100 | 100 | 100 | 0 | 100 | 0 |
| 7 | 25 | 0 | 0 | 0 | 0 | 0 | 0 | 0 | 100 | 0 |
| | 50 | 0 | 0 | 0 | 90 | 90 | 100 | 0 | 0 | 0 |
| 8 | 50 | 0 | 100 | 100 | 100 | 100 | 100 | 100 | 100 | 0 |
| | 50 | 0 | 100 | 100 | 0 | 100 | — | 100 | 100 | 0 |
| 9 | 50 | 50 | 100 | 100 | 95 | 100 | 100 | 100 | 100 | 0 |
| 10 | 50 | 0 | 100 | 100 | 100 | 100 | 100 | 100 | 100 | 0 |
| 11 | 50 | 50 | 100 | 100 | 90 | 100 | 0 | 100 | 90 | 0 |
| 12 | 50 | 0 | 0 | 0 | 0 | 100 | 0 | 95 | 0 | 0 |
| 13 | 25 | 0 | 75 | 50 | 0 | 100 | 0 | 90 | 50 | 0 |
| 14 | 25 | 0 | 0 | 0 | 0 | 0 | 0 | 50 | 0 | 0 |
| 15 | 25 | 0 | 75 | 50 | 0 | 100 | 0 | 75 | 0 | 0 |
| 16 | 25 | 0 | 0 | 0 | 0 | 0 | 0 | 0 | 0 | 0 |

EXAMPLE 6

Agricultural Fungicide Evaluations of Compounds

The compounds of this invention were tested for fungicidal activity in vivo against cucumber downy mildew (CDM), rice blast (RB), *Septoria glume* blotch of wheat (SNW), tomato late blight (TLB), wheat powdery mildew (WPM) and wheat leaf rust (WLR) and the results are shown in Table 4. In tests on cereals (except for rice plants used for testing rice blast), the plants are trimmed about 24 hours prior to the application of the fungicide compound to provide a uniform plant height and to facilitate uniform application of the compound and inoculation with the fungus. The compounds were dissolved in a 2:1:1 mixture of water, acetone, and methanol, sprayed onto the plants, allowed to dry (four to six hours), and then the plants were inoculated with the fungus. Each test utilized control plants which were sprayed with the water, acetone, and methanol mixture and inoculated with the fungus. The remainder of the technique of each of the tests is given below and the results are reported as percent disease control (percentages of plants treated with the compounds of the present invention lacking disease signs or symptoms compared to the untreated control plants).

Cucumber Downy Mildew (CDM)

*Pseudoperonospora cubensis* was maintained on leaves of live Marketer cucumber plants in a constant temperature room at 65° F. to 75° F. in humid air with moderate light intensity for 7 to 8 days. A water suspension of the spores from infested leaves was obtained and the spore concentration was adjusted to about 100,000 per ml of water.

Marketer cucumber seedlings were inoculated by spraying the underside of the leaves with a DeVilbiss atomizer until small droplets were observed on the leaves. The inoculated plants were incubated in a mist chamber for 24 hours at about 70° F. and then subsequently incubated for 6 to 7 days in a controlled temperature room under mist at 65° F. to 75° F. Seven days after inoculation, the percent disease control was determined.

Rice Blast (RB)

Nato rice plants were inoculated with *Piricularia oryzae* (about 20,000 conidia per ml) by spraying the leaves and stems with an airbrush until a uniform film of inoculum was observed on the leaves. The inoculated plants were incubated in a humid environment (75° F. to 85° F.) for about 24 hours, then placed in a greenhouse environment (70° F. to 75° F.). Seven to eight days after inoculation, the percent disease control was determined.

Tomato Late Blight (TLB)

Phytophthora infestans was cultured on four week old Pixie tomato plants in a controlled environment room (65° F. to 70° F. and 100% relative humidity). After storage, the spores were washed from the leaves with water and dispersed by DeVilbiss atomizer over three week old Pixie tomato plants which had been sprayed previously with experimental fungicides. The inoculated plants were placed in a humidity cabinet at 70° F. and constant mist for 24 hours for infection. The plants were then moved to the controlled environment room as above and scored after three more days incubation. Disease control levels were recorded as percent control four days after inoculation and five days after spraying the compounds.

Wheat Powdery Mildew (WPM)

*Erysiphe graminis* (f. sp. *tritici*) was cultured on Pennol wheat seedlings in a controlled temperature room at 65° F. to 75° F. Mildew spores were shaken from the culture plants onto Pennol wheat seedlings which had been sprayed previously with the fungicide compound. The inoculated seedlings were kept in a controlled temperature room at 65° F. to 75° F. and subirrigated. The percent disease control was rated 8 to 10 days after the inoculation.

Wheat Leaf Rust (WLR)

*Puccinia recondita* (f. sp. *tritici* Races PKB and PLD) was cultured on seven day old wheat (cultivar Fielder) over a 14 day period in the greenhouse. Spores were collected from the leaves with a cyclone vacuum or by settling on aluminum foil. The spores were cleaned by sieving through a 250 micron opening screen and stored or used fresh. Storage employed sealed bags in an Ultralow freezer. When stored, spores must be heat shocked for two minutes at 40° F. before use. A spore suspension is prepared from dry uredia by adding 20 mg (9.5 million) per ml of Soltrol oil. The suspension is dispensed into gelatin capsules (0.7 ml capacity) which attache to the oil atomizers. One capsule is used per flat of twenty of the two inch square pots of seven day old Fielder wheat. After waiting for at least 15 minutes for the oil to evaporate from the wheat leaves, the plants are placed in a dark mist chamber (18°-20° C. and 100% relative humidity) for 24 hours. The plants are then put in the greenhouse for the latent period and scored after 10 days for disease levels. Protective and curative tests were inoculated one day after and two days, respectively, before spraying the plants with the test chemicals.

TABLE 4

Green House Test Results of Plant Diseases Control

| Compound | Rate (ppm) | % Control CDM | RB | SNW | TLB | WLR | WPM |
|---|---|---|---|---|---|---|---|
| 1 | — | — | — | — | — | — | — |
| 2 | 600 | — | — | — | 50 | 0 | 0 |
| 3 | 200 | 99 | 90 | — | 80 | 50 | 50 |
| 4 | 200 | 95 | 90 | 50 | 80 | 50 | 0 |
| 5 | 200 | 99 | 95 | 0 | 90 | 80 | 0 |
| 6 | — | — | — | — | — | — | — |
| 7 | 200 | 0 | 0 | 0 | 0 | 0 | 0 |
| 8 | 200 | 0 | 90 | 0 | 0 | 0 | 0 |
| 9 | 200 | 85 | 0 | 0 | 0 | 0 | 0 |
| 10 | 200 | 50 | 50 | 0 | 0 | 0 | 50 |
| 11 | 200 | 95 | 90 | 0 | 80 | — | 0 |
| 12 | — | — | — | — | — | — | — |
| 13 | 200 | 85 | 0 | 0 | 0 | 50 | 50 |
| 14 | 200 | 0 | 0 | 0 | 0 | 0 | 85 |
| 15 | 200 | 0 | 0 | 0 | 0 | 0 | 0 |
| 16 | 200 | 0 | 0 | 0 | 0 | 0 | 0 |

What is claimed is:

1. A compound of the formula 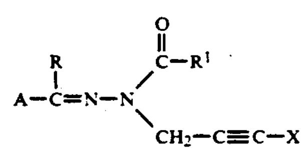 (I)

wherein

A is selected from the group consisting of (1) phenyl, (2) naphthyl, (3) phenyl substituted with one or more halo, cyano, $(C_1-C_4)$alkyl, nitro, $(C_1-C_4)$haloalkyl, and $(C_1-C_4)$thioalkyl, (4) naphthyl substituted with one or more halo, cyano, $(C_1-C_4)$alkyl, nitro, $(C_1-C_4)$haloalkyl, and $(C_1-C_4)$thioalkyl, (5) thiophene, (6) furan, (7) thiophene substituted with one or more substituents selected from halo and nitro, and (8) furan substituted with one or more substituents selected from halo and nitro;

R is selected from the group consisting of hydrogen, $(C_1-C_4)$alkyl and substituted or unsubstituted phenyl wherein the substituents are selected from one or more halo, cyano, $(C_1-C_4)$alkyl, nitro, $(C_1-C_4)$haloalkyl, and $(C_1-C_4)$thioalkyl;

$R^1$ is selected from the group consisting of $(C_1-C_4)$ alkoxy hydrogen; optionally substituted phenyl wherein the phenyl substituents are selected from the group consisting of halo,cyano, $(C_1-C_4)$alkyl, nitro, $(C_1-C_4)$haloalkyl, and $(C_1-C_4)$thioalkyl; $(C_1-C_8)$ alkyl; and optionally substituted heterocycles wherein said heterocycles are selected from the group consisting of thiophene, furan, imidazole, and triazole, which are optionally substituted with $(C_1-C_3)$alkyl, halo, and nitro; and X is selected from the group consisting of I and Br.

2. Compound according to claim 1 wherein A is selected from the group consisting of phenyl, phenyl substituted with halo or nitro, and furan substituted with nitro.

3. Compound according to claim 2 wherein X is I.

4. Compound according to claim 1 wherein R is hydrogen and $R^1$ is selected from the group consisting of hydrogen, $(C_1-C_4)$alkoxy, and phenyl.

5. Compound according to claim 1 wherein A is selected from the group consisting of phenyl, phenyl substituted with halo or nitro, and furan substituted with nitro; R is hydrogen; $R^1$ is selected from the group consisting of hydrogen, $(C_1-C_4)$alkoxy, and phenyl; and X is I.

6. Compound according to claim 1 selected from the group consisting of N'-methoxycarbonyl-N'-3-bromopropargyl 4-chloro-benzaldehyde hydrazone; N'-formyl-N'-3-bromopropargyl 4-chlorobenzaldehyde hydrazone; N'-methoxycarbonyl-N'-3-iodopropargyl benzaldehyde hydrazone; N'-methoxycarbonyl-N'-3-iodopropargyl 4-methylbenzaldehyde hydrazone; N'-methoxycarbonyl-N'-3-iodopropargyl 4-chlorobenzaldehyde hydrazone; N'-benzoyl-N'-3-iodopropargyl benzaldehyde hydrazone; N'-methoxycarbonyl-N'-3-bromopropargyl 4-fluorobenzaldehyde hydrazone; N'-methoxycarbonyl-N'-3-iodopropargyl 5-nitro-2-furancarboxaldehyde hydrazone; N'-methoxycarbonyl-N'-3-iodopropargyl 4-cyanobenzaldehyde hydrazone; N'-methoxycarbonyl-N'-3-iodopropargyl 4-fluorobenzaldehyde hydrazone; N'-methoxycarbonyl-N'-3-iodopropargyl 3,4-dichlorobenzaldehyde hydrazone; N'-benzoyl-N'-3-iodopropargyl 3-nitrobenzaldehyde hydrazone; N'-ethoxycarbonyl-N'-3-iodopropargyl 3,4-dichlorobenzaldehyde hydrazone; N'-ethoxycarbonyl-N'-3-bromopropargyl 3,4-dichlorobenzaldehyde hydrazone; N'-methoxycarbonyl-N'-3-iodopropargyl 3,5-dichlorobenzaldehyde hydrazone; N'-methoxycarbonyl-N'-3-bromopropargyl 3,5-dichlorobenzaldehyde hydrazone.

7. Composition comprising a compound according to claim 1 and an agronomically acceptable carrier.

8. Composition comprising a compound according to claim 1 and a stabilizer.

* * * * *